United States Patent [19]

Bargigia et al.

[11] Patent Number: 4,654,448

[45] Date of Patent: Mar. 31, 1987

[54] PROCESS FOR THE SYNTHESIS OF HEXAFLUOROBUTADIENE AND OF HIGHER PERFLUORINATED DIENES

[75] Inventors: Gianangelo Bargigia; Vito Tortelli, both of Milan; Claudio Tonelli, Concorezzo, all of Italy

[73] Assignee: Ausimont S.p.A., Milan, Italy

[21] Appl. No.: 867,694

[22] Filed: May 28, 1986

[30] Foreign Application Priority Data

May 29, 1985 [IT] Italy ............................ 20935 A/85

[51] Int. Cl.[4] ........................................... C07C 17/24
[52] U.S. Cl. ................................. 570/156; 570/157; 570/158
[58] Field of Search ..................... 570/156, 157, 158

[56] References Cited

FOREIGN PATENT DOCUMENTS 2028328  3/1980  United Kingdom ............... 570/158

Primary Examiner—Natalie Trousof
Assistant Examiner—Joseph A. Boska
Attorney, Agent, or Firm—Stevens, Davis, Miller & Mosher

[57] ABSTRACT

Perfluorobutadiene and higher perfluoroalkadienes, with terminal double bonds, are obtained from $\alpha,\omega$-diiodoperfluoroalkanes by deiodofluorination realized by using an organometallic compound, in the presence either of an aprotic solvent belonging to the class of hydrocarbons, or of an aprotic polar solvent, with short reaction times.

4 Claims, No Drawings

PROCESS FOR THE SYNTHESIS OF HEXAFLUOROBUTADIENE AND OF HIGHER PERFLUORINATED DIENES

BACKGROUND OF THE INVENTION

1. Field of the Invention

The present invention relates to a process for the synthesis of perfluorobutadiene and of higher perfluoroalkadienes with terminal double bonds, by a reaction of $\alpha,\omega$-diiodo-perfluoroalkanes deiodofluorination carried out by using organometallic compounds.

2. Description of the Prior Art

Perfluorobutadiene is a chemically interesting compound, because it has been proposed for use as termonomer, in smaller amount, together with $CF_2=CH_2$ and $CF(CF_3)=CF_2$ to produce fluoroelastomers vulcanizable by peroxides (Daikin's Japanese Pat. No. 47,752 publ. July 7th, 1977). It has also been proposed for use as termonomer together with $C_2F_4$ and trifluoronitrosomethane to manufacture another curable fluorinated elastomer (see German Pat. No. 2,304,650 and J. Chem. Soc. Perkin I, 1973, page 1111). In fact, in these copolymers, perfluorobutadiene enters by polymerizing in 1-2 position, thus leaving one double bond unaltered and available for crosslinking reactions.

Another use of perfluorobutadiene (see U.S. Pat. No. 3,980,509) is as bonding agent, in polymer form, in "fluoro-oxidizer systems", wherein such polymer acts both as bonding agent and as fuel, while a fluoride salt, such as $NH_4BF_4$ acts as the oxidizer (see J. Appl. Polymer Sci. 19 (1975) 1359).

Another patent (U.S. Pat. No. 3,353,904) mentions perfluoropolyenes having terminal double bonds as agents to confer water-repellency characteristics to cotton.

Although perfluorobutadiene is considered as a very valuable product, the development of the products which can be obtained from it has been limited by the fact that a synthesis, suitable to be realized on full industrial scale, of such compound, was not available.

The processes known so far for the synthesis of perfluorobutadiene and of higher perfluorodienes are briefly mentioned hereunder.

In U.S. Pat. No. 3,046,304, the starting products are ICl and $CClF=CF_2$. From the mutual reaction of these compounds $CClFI—CClF_2$ is obtained, which in its turn dimerizes, with a yield of 82%, in the presence of an equal volume of elemental mercury, $CClF_2—CFCl—CFCl—CClF_2$ being obtained, which in its turn can be dechlorinated by Zn powder in ethyl alcohol to perfluorobutadiene, with a yield of 98%.

This synthesis has the drawback that it can be accomplished only difficultly on industrial scale, because in the dimerization a large amount of mercury must be used, and the reaction mixture must be strongly stirred: thus, severe problems must be faced as for environmental pollution and equipment. Moreover, in the subsequent dechlorination step, the problem occurs of dispersing the Zn powder into the liquid reaction phase, which creates considerable difficulties. Finally, the first process step, i.e., the reaction of $CClF=CF_2$ with ICl, requires extremely long reaction times (6 weeks) and yields are rather low (72,6%), see C.A. 74 (1971) 126097 h.

Higher perfluorodienes, such as, e.g., 1,5-perfluorohexadiene, are obtained by starting from above mentioned $CF_2Cl—CFClI$, by telomerization of $C_2F_4$ in the presence of $\gamma$-radiation and under high pressure, the telomer $CF_2ClCFCl(C_2F_4)_2I$ being obtained, which is subsequently chlorinated with chlorine in the presence of U.V. rays, and then dehalogenated in two steps. In the first step, accomplished with Zn powder in acetic acid+acetic anhydride mixture, a double bond is formed by dechlorination, and in the second step, carried out with Zn powder in diethylene glycol, the dechlorofluorination occurs, with the formation of the second double bond (see C.A. 74 (1971) 126097 h).

This method is complex due to the many reaction steps it requires, and its overall yield is very poor: moreover, the use of $\gamma$-rays in an industrial process is complex and unproposable.

Finally, a method is known (see C.A. 98 (1983) 126788 e) for preparing perfluorobutadiene by starting from $BrClFC—CBrF_2$, which is added (by telomerization) to $ClFC=CF_2$ in the presence of U.V. radiation, $BrF_2C—CClF—CClF—CBrF_2$ being obtained. This latter is dehalogenated with Zn powder in acetic acid+acetic anhydride. The method cannot be applied to higher perfluoroalkadienes. For this process too, the difficulties are considerable to an industrial implementing, because of use of U.V. rays and Zn powder. Furthermore, the synthesis of the brominated $C_4$ intermediate occurs with low yields as referred to $CClF=CF_2$.

THE PRESENT INVENTION

The object of the present invention is a process for the preparation of perfluoroalkadienes having general formula:

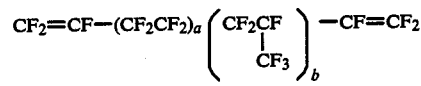

wherein a is an integer from 0 to 3, preferably from 0 to 2; b is an integer from 0 to 2, the sum of a+b is comprised within the range of from 0 to 4, and the units with a and b subscript can also be alternate with each other; which comprises the deiodofluorination of $\alpha,\omega$-diiodoperfluoroalkanes of general formula:

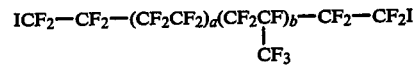

carried out with an organometallic compound, in the presence of an aprotic solvent belonging to the class of hydrocarbons, or of a polar aprotic solvent belonging to the class of ethers and cyclic ethers, or of mixtures thereof. As the organometallic compound, an alkylmagnesium or arylmagnesium halide, a dialkylmagnesium or a diarylmagnesium, zinc and cadmium alkyl compounds, an alkyllithium or an aryllithium can be used. In the case of perfluorohexadiene preparation, using an alkyllithium is preferable.

In general, the organometallic compounds are used as solutions in ether solvents, in case of Li or Cd organometallic compounds solutions of the same in ethers or hydrocarbon solvents are used.

Preferred solvents are dioxane, ethyl ether, tetrahydrofuran, diethyleneglycol dimethylether, dimethoxyethane, hexane, octane, petroleum ether.

The reaction temperature is generally comprised within the range of from $-80°$ C. to $+150°$ C.

The reactants can be used in stoichiometric molar ratio, or with the organometallic compound being present in an amount slightly higher or lower than stoichiometric.

The diiodoperfluoroalkanes used as the starting products are known products, which can be obtained by the reaction of $C_2F_4$ with $I_2$ and subsequent telomerization of $C_2F_4$ with $ICF_2CF_2I$ formed. The telomerization can be carried out also by a mixture of $C_2F_4$ and $CF(CF_3)=CF_2$ according to processes disclosed in Italian Patent Appln. No. 20235 A/85 to the same applicant.

The deiodofluorination reaction must be carried out under specific operating conditions, in particular directed to prevent as far as possible the end product from coexisting in the reaction medium with the reactants and the byproducts formed. Suitably, besides keeping the reation time as short as possible, of the order of 30 minutes, or even less if the evolving of the gaseous reaction products can be kept successfully controlled, also the removal from the reaction medium should be carried out of the end product as it is formed, either by a stream of inert gas, or by distilling the reaction solvent under room pressure or under reduced pressure. In this latter case, the end product is entrained by the solvent during the distillation.

As it has already been said in the foregoing, for the reaction to proceed correctly, it is essential that the reacting diiodoperfluoroalkane be dissolved in a suitable solvent selected from those previously mentioned.

A suitable practical operating way consists in admixing the solution of organometallic compound at concentration of from 0.2 to 2.5 and preferably of from 0.5 to 1.5 molar in the above mentioned solvents, with a solution of diiodoperfluoroalkane in a solvent of the same type or also in a different solvent, which must be inert towards the organometallic compound, e.g., hexane.

The following examples are supplied to the purpose of illustrating the invention, without limiting the scope thereof.

EXAMPLE 1

Into a 150-ml flask equipped with magnetic stirrer, dripping funnel, thermometer, reflux condenser connected to a trap at $-80°$ C., 11.4 g of $I(C_2F_4)_2I$ (0.025 mol) in 50 ml of tetrahydrofuran (THF) is charged.

The whole is heated to boiling temperature, and 50 ml of 1M solution of $C_2H_5MgBr$ (0.05 mol) in ethyl ether is introduced at such a rate as to allow the effervescence caused by the reaction to be controllable. The gases released are condensed in the trap at $-80°$ C.

An amount of 2.9 g is collected of colourless liquid which on gas-chromatographic analysis (G.C.) shows one single peak, and which by N.M.R. and I.R. analyses, and on the basis of its boiling point, is identified as

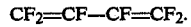
$CF_2=CF-CF=CF_2$.

In the reactor, together with the reaction solvent, a further amount of 1.0 g of perfluorobutadiene remains. The yield results hence of 96%.

EXAMPLE 2

Into a reactor similar to that of Example 1, 13.8 g of $I(C_2F_4)_2I$ (0.03 mol) in 80 ml of anhydrous ethyl ether is introduced. After cooling to $-80°$ C., a 1.6M solution of butyllithium (0.06 mol) in hexane is added, with the addition rate being so adjusted that the temperature of the reaction mass never exceeds $-70°$ C.

The reaction mass is allowed to spontaneously warm up to room temperature, and is then heated to boiling temperature. A gaseous product (identified as perfluorobutadiene) is released and collected at $-80°$ C. in an amount of 4.75 g.

Inside the boiler, together with the solvent, the butyl iodide equivalent to the butyllithium used remains.

The yield results to be 97.5%.

EXAMPLE 3

Into a reactor similar to that of Example 1, with the difference that the condenser is replaced by a 25-cm high Vigreux column provided with head with refluxing rate adjusting means, 36 g of $I(C_2F_4)_3I$ (0.065 mol) in 60 ml of anhydrous ethyl ether is charged. Into the dripping funnel 100 ml is charged of a 1.3M solution of butyllithium (0.13 mol) is ethyl ether. The whole is cooled to $-80°$ C. and 70 ml of the solution of $C_4H_9Li$ is added; the reaction mass is allowed to warm up to room temperature and is then heated to boiling temperature, about 130 ml of distillate being collected.

Into the reactor further 20 ml of ether is introduced, the reaction mass is cooled to $-80°$ C., and the residual 30 ml of butyllithium solution is added dropwise.

The reaction mass is distilled until inside the reactor only solid products and a few drops of liquid remain.

The distillate is rectified, the most of the ether being removed. The residue is extracted in continuous with water, to completely eliminate ether.

At the end, two layers are obtained; the lower layer weighs 17 g, and upon G.C. analysis shows, in the order, the following peaks: a main peak, equal to 76%; a peak with shoulder equal to 21%, and other minor peaks.

N.M.R.($^{19}$F) and mass-spectrometric analyses confirm the main product to be

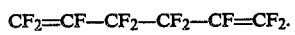
$CF_2=CF-CF_2-CF_2-CF=CF_2$.

The chemical shifts are at ($\delta$, ppm, $CCl_3F$) 88, 105, 119.5, 190, with integration ratio of respectively 1:1:2:1.

On gas mass the molecular ion (M=262) is identified, and the main fragments have mass 243 (M—F), 181 (M—$C_2F_3$), 131 (the most intense peak, equal to M/2).

EXAMPLE 4

Into a reactor similar to that of example 3, 16.3 g of $I(C_2F_4)_4I$ (0.025 mol) in 50 ml of anhydrous dioxane is charged.

The solution is heated to boiling temperature and over a 20 minutes time, 50 ml (0.05 mol) of 1M $C_2H_5MgBr$ solution in THF is added.

In the cold trap a mixture of solvent, of $C_2H_5I$ and of fluorinated products is collected.

The mixture obtained is extracted 4 times by using a large excess of water, so to remove the most of the organic solvent. The extraction residue is cooled to $-20°$ C.; two layers are formed, the weight of the lower layer being of 6.4 g.

On N.M.R.($^{19}$F) analysis shifts are observed at ($\delta$, ppm, $CCl_3F$) 88, 105, 118, 123, 189.5. On the basis of the large number of signals and of the integration, to the product the structure:

$CF_2=CFCF_2CF_2CF_2CF_2CF=CF_2$ is assigned.

The yield results of 71% in 1,7-perfluorooctadiene. N.M.R. analysis of the residue in the boiler does not show any presence of the iodide used as reactant.

COMPARATIVE EXAMPLE

Into the reactor of Example 1, a sample of 11.3 g of pure I(C$_2$F$_4$)$_2$I (0.025 mol) is introduced and is heated to 50° C.; the heat source is then removed.

An amount of 52 ml of 1.1M solution of C$_2$H$_5$MgBr in THF is rapidly added dropwise. Exothermicity and effervescence is observed.

The product collected in the cold trap, purified of solvent traces, weighs 2 g and is constituted by 83% of perfluorobutadiene and 17% of cyclobutene.

This latter is identified by N.M.R. and chromatographic analysis associated to mass spectrometry; perfluorobutadiene is identified by comparing its I.R. and N.M.R. spectra with those known from technical papers. In the reactor no presence of perfluorobutadiene is observed any longer. t The yield in perfluorobutadiene is of 41%.

What is claimed is:

1. Process for the preparation of perfluoroalkadienes having general formula:

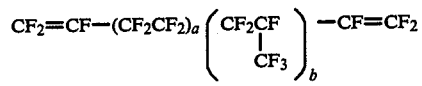

wherein a is an integer from 0 to 3; b is an integer from 0 to 2, the sum of a+b is comprised within the range of from 0 to 4, and the units with a and b subscript can also be alternate with each other; which comprises the deiodofluorination of α,ω-diiodoperfluoroalkanes of general formula:

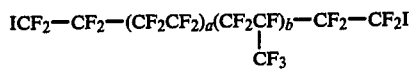

carried out by the reaction of an organometallic compound of Mg, Zn, Cd or Li, carried out in the presence of an aprotic solvent belonging to the class of hydrocarbons, or of a polar aprotic solvent belonging to the class of ethers and cyclic ethers, at a temperature comprised within the range of from −80° C. to +150° C.

2. Process according to claim 1, furthermore characterized in that the product obtained is removed from the reaction mixture during the proceeding of the same reaction, by distillation together with the reaction solvent or by a flow of inert gas.

3. Process according to claim 1, characterized in that the organometallic compound is selected from: alkylmagnesium or arylmagnesium halides, dialkylmagnesium, diarylmagnesium, zinc and cadmium alkyl compounds, an alkylithium or an aryllithium.

4. Process according to claim 1, wherein perfluorohexadiene is obtained, and as the organometallic compound an alkyllithium is used.

* * * * *